United States Patent [19]
Granger et al.

[11] 3,979,284
[45] Sept. 7, 1976

[54] ARTIFICIAL HAEMODIALYSIS KIDNEYS

[75] Inventors: Alain Granger, Lesigny; André Sausse, Sceaux, both of France

[73] Assignee: Rhone-Poulenc S.A., Paris, France

[22] Filed: Mar. 21, 1975

[21] Appl. No.: 560,861

Related U.S. Application Data

[63] Continuation of Ser. No. 384,286, July 31, 1973, abandoned.

[30] Foreign Application Priority Data

July 31, 1972 France .............................. 72.27582

[52] U.S. Cl. ........................... 210/22 A; 210/321 B
[51] Int. Cl.² .................. B01D 31/00; B01D 13/00
[58] Field of Search ...................... 210/22, 321, 416

[56] References Cited
UNITED STATES PATENTS 3,669,880   6/1972   Marantz et al .................. 210/321 X 3,795,318   3/1974   Crane et al. ........................ 210/321

*Primary Examiner*—Frank A. Spear, Jr.
*Attorney, Agent, or Firm*—Cushman, Darby & Cushman

[57] ABSTRACT

An artificial haemodialysing kidney and method of operation in which the haemodialyser has one chamber connectable to a blood stream and another chamber on the opposite side of its membrane forming part of a constant volume closed vessel for dialysis liquid. The system can be operated as a closed circuit during which time a fraction of the dialysis liquid is withdrawn from the constant volume closed vessel at a desired flow rate and the reduction in pressure then existing in the vessel near the membrane is noted. The system is then switched to open circuit with the dialysis liquid being fed from a source thereof and the used liquid is dumped, the pressure during this period being adjusted to the noted value.

3 Claims, 4 Drawing Figures

ARTIFICIAL HAEMODIALYSIS KIDNEYS

This is a continuation of application Ser. No. 384,286 filed July 31, 1973, now abandoned.

The present invention relates to artificial haemodialysis kidneys.

It has previously been shown that artificial kidneys having an open circuit haemodialyser do not permit the ultrafiltration flow to be conveniently judged. A closed circuit haemodialyser has been described in our copending Application Ser. No. 312,515 filed Dec. 6, 1972., now U.S. Pat. No. 3,939,069 the disclosure of which is incorporated herein by reference, and which permits the ultrafiltration to be measured with precision.

According to the invention, we provide an artificial haemodialysis kidney comprising, a source of dialysis liquid; a haemodialyser including a membrane capable of permitting simultaneous dialysis and ultrafiltration of blood; a chamber on one face of said membrane connectable to a blood stream; a constant volume closed vessel in the form of a loop, having a wall portion formed by a second face of said membrane, said vessel containing a dialysis liquid; a circulation pump in said loop downstream of the dialyser, means for withdrawing from said constant volume closed vessel, at a predetermined rate, a fraction of the dialysis liquid; a two position valve system, movable between a first position in which simultaneously the source of liquid is connected to the constant volume closed vessel to direct said liquid to said membrane and the liquid having passed said membrane is directed in open circuit to the exterior, and a second position which simultaneously isolates the constant volume closed vessel from the source and from the exterior to form a closed circuit for the dialysis liquid, and means for adjusting the pressure difference on either side of the membrane.

If desired, a second valve system may be provided which is capable of placing into circuit a device, for example of a kind described in our said earlier Application, for regenerating the dialysis bath, so as to make the dialyser totally independent from its source of dialysis liquid in case of need.

The arrangement according to the invention enables the ultrafiltration flow to be controlled at any instant. Thus it enables the pressure of the dialysis liquid to be adjusted, either so as to modify the flow of ultrafiltration or to keep it constant despite variation of blood pressure or of permeability of the membrane.

It suffices, in fact, to cause the kidney to function in closed circuit with withdrawal of the flow corresponding to the desired ultrafiltration and to note the pressure of the dialysis liquid near the dialyser. The apparatus is then restored to open circuit and one adjusts for example the tap admitting fresh dialysis liquid so that the reduced pressure created by the circulation pump corresponds to the value which has been established in closed circuit.

Thus, according to another aspect of the invention we provide a method of dialysis together with ultrafiltration of a liquid comprising providing a constant volume closed vessel having a wall portion forming a membrane of a dialysis and ultrafiltration apparatus, connecting the face of said membrane remote from said constant volume closed vessel to the liquid to be dialysed and ultrafiltered, filling said vessel with a dialysis liquid, withdrawing a fraction of said dialysis liquid from the vessel at a predetermined desired flow rate, noting the reduction in pressure then existing in the constant volume closed vessel near the membrane, switching the operation of said system into open circuit and adjusting the reduced pressure to the value noted.

During the measuring in closed circuit it is possible to regenerate the dialysis liquid by any known method. However, it has been observed that the dialysis liquid can be once or twice recycled before a substantial reduction of the performance of the apparatus is brought about and that in any event only the flow of fresh liquid counts, rather than the number of recycles. It is thus sufficient if the circuit has a capacity which is adequate for the duration of a control not to bring about an excessive reduction of the dialysis efficiency. Thus, with a circulation flow of 500 ml/min. a capacity of 10 liters enables the ultrafiltration flow to be controlled for 10, 20 or 40 min., depending on whether ½, 1 or 2 recycles are accepted.

The invention will be better understood from the following description which is given merely by way of example, reference being made to the accompanying drawings, in which.

Figure 1:
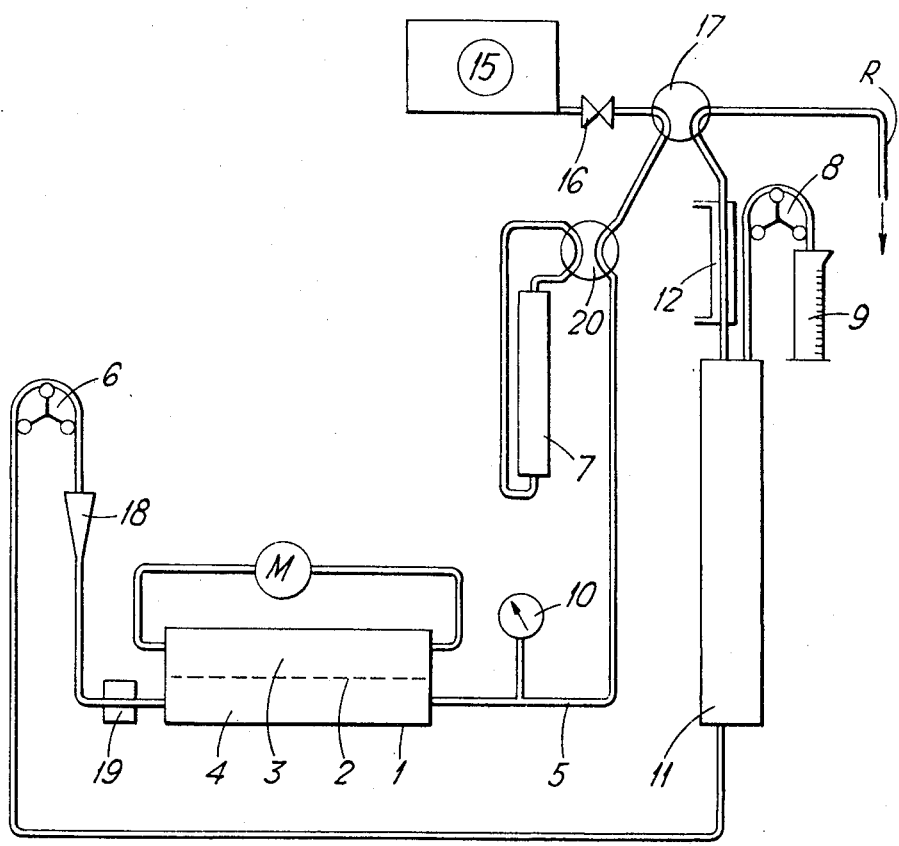
FIG. 1 is a schematic circuit diagram of one embodiment of kidney according to the invention operating normally in open circuit.

According to FIG. 1 the haemodialyser 1 is divided by at least one membrane 2 into a blood compartment 3 connected to the patient M and a dialysis liquid compartment 4.

The membrane may be of any known kind, for example of "copper" regenerated cellulose. Upstream of the compartment 4 there is disposed the source 15 of dialysis liquid which may either be a reservoir containing the diluted dose for an entire treatment or a generator connected to the water mains and diluting a concentrate as required. The source 15 is connected to the dialyser through the intermediary of an adjustment tap 16. A volumetric pump 6 of adjustable throughput positioned downstream of the dialyser ensures the renewal of the bath and produces the reduced pressure which causes the ultrafiltration. A manometer 10 placed in the neighbourhood of the dialyser between the pump 6 and the tap 16 enables the reduced pressure prevailing in the compartment 4 to be estimated. It does not necessarily indicate the true pressure existing at a precise point of the membrane but is sufficient to define the operational conditions in a practical manner.

An artificial kidney operating in open circuit comprises as a rule various attachments, for example a flow meter 18, and a colorimeter 19 downstream (detection of blood leakage).

Figure 2:
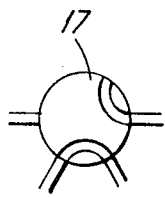
FIG. 2 shows the position of one valve of the kidney of FIG. 1 during closed circuit operation.

According to the invention the bath issuing from the dialyser can be recycled by means of a valve 17 of any convenient type. The case of a four-way switch staggered at 60° is illustrated, the four ways being connected to the source 15, the inlet of the compartment 4, the outlet of this compartment, and waste R for used dialysis liquid respectively. FIG. 1 shows the position of the valve when the kidney operates in open circuit, FIG. 2 shows the position for the operation in closed circuit, the dialysis liquid source 15, being isolated.

Downstream of the compartment 4 the dialysis liquid circuit 5 has a branch through which a volumetric pump 8 of adjustable throughput can draw off the liquid at a flow rate corresponding to the desired ultrafiltration. The extracted quantity can be measured by any appropriate device, for example a calibrated receptacle 9 or an integrator of the speed and thus of the throughput of the pump, as a function of time, which has the advantage of being able to function during the operation in open circuit, whether the pump operates or does not operate. The pump 8 can be stopped during the operation in open circuit or it can function by simulating the ultrafiltration.

A container 11 resistant to crushing by reduced pressure (as is the remainder of the circuit) permits storage in the closed circuit of a constant volume of dialysis liquid which is sufficient for the measuring of the ultrafiltration flow to be applied during a suitable length of time without impairing the quality of the dialysis.

Figure 3:
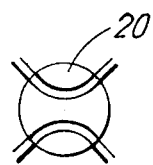
FIG. 3 shows the position of a second valve when the dialysis liquid regenerator is in use.

If desired, the circuit may also comprise a dialysis liquid regenerator 7 connected by a valve 20 having 4 ways at 90°, disconnected in FIG. 1 and placed in series in the circuit according to FIG. 3. The circuit also includes a thermostatic reheater 12.

Figure 4:
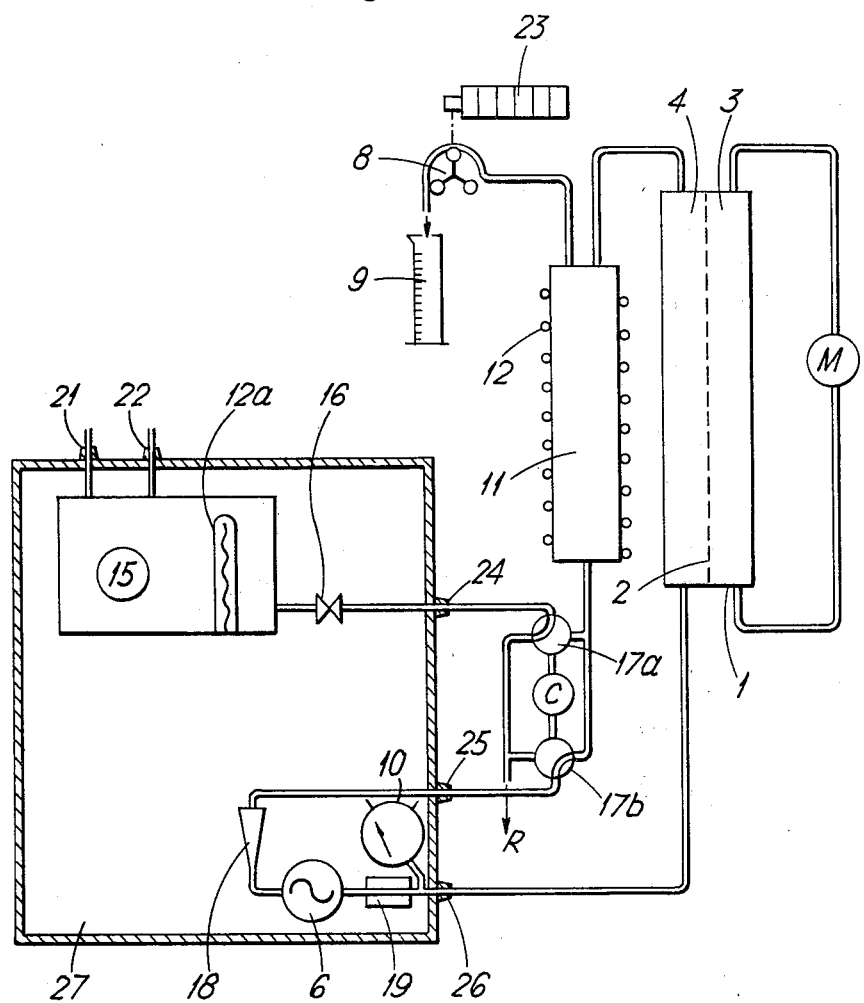
FIG. 4 is a schematic side elevation of a practical embodiment of kidney in its recycling position during an ultrafiltration measurement.

By way of variant FIG. 4 shows a practical embodiment of the circuit of the dialysis bath wherein a "monitor generator" 27 combines a dialysis liquid source 15 with water and concentrate inlets 21 and 22 and a thermostat 12a, an adjustment valve 16, a manometer 10 having "excessive pressure/too low pressure" contacts, a colorimeter 19, a flow meter 18 and a circulation pump 6 in the form of a compact assembly, generally a closed box having three connections, namely a supply connection 24 for the fresh dialysis liquid a return connection 26 for the used dialysis liquid toward the circulation pump, and an exit connection 25 for the used bath.

According to this variant the reservoir 11 and the valve 17 are directly interposed between the monitor (connections 24 and 25) and the inlet of the dialyser, which necessitates virtually no modification of a standard apparatus.

There is here shown a valve consisting of two taps 17a receiving the fresh dialysis liquid and 17b receiving the used dialysis liquid, connected by a chronometric (c) or manual control means. Sliding valve distributors could alternatively be used.

A summing revolution counter 23 enables the total volume of ultrafiltrate to be calculated, the pump 8 rotating permanently and simply acting as an integrator during the running in open circuit.

When the dialysis liquid source 15 is of the continuous flow kind the bath unused during a measuring of the ultrafiltration flow can simply be rejected to the exterior (R) as is shown in FIG. 4.

In FIGS. 1 and 4, the manometer 10 is connected only to the conduit 5 which corresponds to the side of the membrane in contact with the path. In effect the pressure of blood on the other face of the membrane is practically constant. It is sufficient to take into account this pressure at the time of calibrating the manometer or at the time of reading of the pressure.

We claim:
1. An artificial haemodialysis kidney comprising, in combination:
   a. A source of dialysis liquid;
   b. a haemodialyser including a membrane capable of permitting simultaneous dialysis and ultrafiltration of blood;
   c. a chamber on one face of said membrane connectable to a blood stream;
   d. a constant volume closed system in the form of a closed loop having a wall portion formed by a second face of said membrane, said system containing a dialysis liquid;
   e. a circulation pump in said loop downstream of the dialyser;
   f. means for withdrawing by pumping from said constant volume closed system, at a predetermined rate, a fraction of the dialysis liquid so that the volume of liquid in said system is maintained constant;
   g. a two position valve system, movable between a first position in which simultaneously the source of liquid is connected to the constant volume closed system to direct said liquid to said membrane and the liquid having passed said membrane is directed in open circuit to the exterior, and a second position which simultaneously isolates the constant volume closed system from the source and from the exterior to form a closed circuit for the dialysis liquid; and
   h. means for adjusting the pressure difference on either side of the membrane.

2. An artificial haemodialysis kidney as claimed in claim 1, further comprising a dialysis liquid regenerator and a second valve enabling connection and disconnection of said generator to said constant volume closed system.

3. A method of dialysis together with ultra-filtration of a liquid comprising the steps of providing a constant volume closed system having a wall portion forming a membrane of a dialysis and ultrafiltration apparatus, connecting the face of said membrane remote from said constant volume closed system to the liquid to be dialysed and ultrafiltered, filling said system with a dialysis liquid, circulating the dialysis liquid along said membrane at a flow corresponding to the normal condition of a haemodialysis operation, withdrawing by pumping a fraction of said dialysis liquid from the system at a predetermined desired flow rate, so that the volume of liquid in said system is maintained constant, noting the reduction in pressure then existing in the constant volume closed system near the membrane, switching the operation of said system into open circuit and ajusting the reduced pressure to the value noted.

* * * * *